US012617788B2

(12) United States Patent
Chen et al.

(10) Patent No.: US 12,617,788 B2
(45) Date of Patent: May 5, 2026

(54) BRIDGED BICYCLIC COMPOUNDS AS BTK INHIBITORS

(71) Applicant: Beijing InnoCare Pharma Tech Co., Ltd., Beijing (CN)

(72) Inventors: Xiangyang Chen, Beijing (CN); Yucheng Pang, Beijing (CN)

(73) Assignee: Beijing Innocare Pharma Tech. Co. Ltd., Beijing (CN)

( * ) Notice: Subject to any disclaimer, the term of this patent is extended or adjusted under 35 U.S.C. 154(b) by 531 days.

(21) Appl. No.: 18/169,408

(22) Filed: Feb. 15, 2023

(65) Prior Publication Data

US 2023/0212175 A1 Jul. 6, 2023

Related U.S. Application Data

(63) Continuation of application No. PCT/CN2021/113538, filed on Aug. 19, 2021.

(30) Foreign Application Priority Data

Aug. 20, 2020 (CN) ......................... 202010836243.4

(51) Int. Cl.
*C07D 471/04* (2006.01)
*C07D 487/04* (2006.01)

(52) U.S. Cl.
CPC ......... *C07D 471/04* (2013.01); *C07D 487/04* (2013.01)

(58) Field of Classification Search
CPC ............................ C07D 471/04; C07D 487/04
See application file for complete search history.

(56) References Cited

U.S. PATENT DOCUMENTS

2023/0192691 A1* 6/2023 Chen ....................... A61P 19/08 514/233.2

FOREIGN PATENT DOCUMENTS

| | | |
|---|---|---|
| CN | 108431007 A | 8/2018 |
| CN | 110291080 A | 9/2019 |
| WO | 2013/010380 | 1/2013 |
| WO | 2016/019237 | 2/2016 |
| WO | 2016/106623 | 7/2016 |
| WO | 2016/106624 | 7/2016 |
| WO | 2016/106652 | 7/2016 |
| WO | 2020/015735 A1 | 1/2020 |
| WO | 2020/063012 A1 | 4/2020 |
| WO | 2020/150681 A1 | 7/2020 |
| WO | 2021/184154 A1 | 9/2021 |
| WO | 2021/188417 A1 | 9/2021 |
| WO | 2022/037649 A1 | 2/2022 |

OTHER PUBLICATIONS

Extended European Search Report mailed Sep. 19, 2024 in EP Application No. 21857742.7, 7 pages.
International Search Report for PCT Application No. PCT/CN2021/113538, filed Aug. 19, 2021, mailed Nov. 17, 2021, 13 pages.
Gao, Xiaolei, et al. "Discovery of novel BTK inhibitors with carboxylic acids" Bioorganic & Medicinal Chemistry Letters 25, Nov. 2016(Nov. 25, 2016) vol. 27 pp. 1471-1477.

* cited by examiner

*Primary Examiner* — Erich A Leeser
(74) *Attorney, Agent, or Firm* — Viola Kung; Perkins Coie LLP

(57) ABSTRACT

The present invention relates to bridged bicyclic Compounds A and B or their pharmaceutically acceptable salts thereof as inhibitors of Bruton's tyrosine kinase (BTK) and its C481 mutant. The present invention also relates to methods for preparing Compounds A and B or their pharmaceutically acceptable salts thereof. Compounds of the present invention can be used to treat and/or prevent related diseases mediated by BTK or its C481 mutant, especially cancer and autoimmune diseases.

A

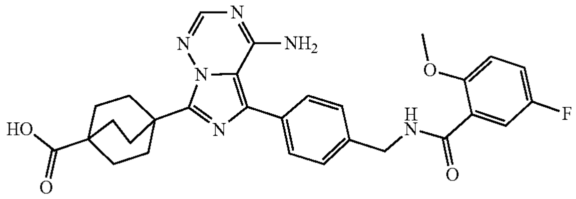

B

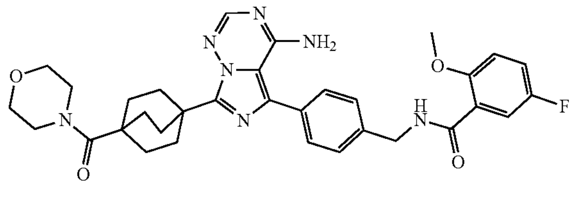

5 Claims, No Drawings

BRIDGED BICYCLIC COMPOUNDS AS BTK INHIBITORS

This application is a continuation of PCT/CN2021/113538, filed Aug. 19, 2021, which claims the priority of Chinese Application No. 202010836243.4, filed Aug. 20, 2020. The contents of the above-identified applications are incorporated herein by reference in their entireties.

TECHNICAL FIELD

The invention relates to bridged bicyclic compounds or their pharmaceutically acceptable salts thereof, suitable for regulating or inhibiting activities of Bruton tyrosine kinase (BTK) and its C481 mutant. The present invention also relates to methods for preparing the compounds or their pharmaceutically acceptable salts thereof. The present invention further relates to the uses and methods of use of the compounds or their pharmaceutically acceptable salts thereof in the treatment and/or prevention of cancer and autoimmune diseases.

BACKGROUND ART

BTK is an important non-receptor tyrosine kinase that mediates cell signal transduction, which exists in plasma cells including B-cells. B-cells are activated through B-cell receptor (BCR) and BTK plays an important role in the BCR-mediated signaling pathway. After BCR on B-cells is activated, it causes the activation of BTK which leads to an increase in the concentration of downstream phospholipase C (PLC) and activates the IP3 and DAG signaling pathways. This signaling pathway can promote cell proliferation, adhesion and survival, and plays an important role in the development of B-cell lymphoma.

BTK inhibitors inhibit the proliferation of B lymphoma cells by inhibiting the activity of BTK, destroy adhesion of tumor cells, and promote tumor cell apoptosis, making BTK a compelling drug target for B-cell related cancers, such as non-Hodgkin's lymphoma (NHL), chronic lymphocytic leukemia (CLL)/small lymphocytic lymphoma (SLL), mantle cell lymphoma (MCL), Waldenstrom's macroglobulinemia (WM), marginal zone Lymphoma (MZL), central nervous system leukemia (CNSL), etc. Several BTK inhibitors are currently on the market, including Abbvie/JNJ's ibrutinib, AZ's acalabrutinib, Beigene's zanubrutinib and Gilead/Ono's tirabrutinib, and more BTK inhibitors are in clinical research.

In addition to treating B-cell associated lymphomas, BTK inhibitors can also inhibit the production of B-cell autoantibodies and cytokines. In autoimmune diseases, B-cells present their own antigens, promote T-cell activation, secrete inflammatory factors that cause tissue damage, and at the same time activate B-cells to produce a large number of antibodies to trigger an autoimmune response. T- and B-cells interact to each other to form a positive feedback regulatory chain which leads to uncontrolled autoimmune responses and aggravates tissue pathological damage. Studies have shown that there are regulatory B-cells in the body which can negatively regulate the immune response and inhibit immune-mediated inflammation through the secretion of interleukin 10 (IL-10) or transforming growth factor β1 (TGF-β1) and other mechanisms. Therefore, BTK can be a drug target for autoimmune diseases, such as rheumatoid arthritis (RA), multiple sclerosis (MS), systemic lupus erythematosus (SLE), pemphigus, etc. For autoimmune indications, BTK inhibitors are still in clinical research. Among them, Sanofi's rilzabrutinib and Merck Serono's evobrutinib have achieved effective results in the treatment of pemphigus and multiple sclerosis, respectively.

Most of BTK inhibitors on the market and under research are irreversible inhibitors which inhibit the activity of BTK by covalently binding to the cysteine residue located at 481 of the BTK protein. After some B-cell lymphoma patients received ibrutinib treatment for a period of time, BTK's C481 mutation, such as C481S, made ibrutinib lose its covalent binding point with the protein, resulting in a decrease in the activity of ibrutinib, thereby making patients resistant to the ibrutinib treatment (Quinquenel, et. al Blood 2019, 134, 641-644).

There exists a need for BTK inhibitors which effectively inhibit the activities of BTK and its C481 mutant, thereby overcoming the drug resistance caused by the C481 mutation associated with irreversible BTK inhibitors.

DETAILED DESCRIPTION OF THE INVENTION

Definitions

Unless otherwise stated, the following terms used in this application have the following meanings.

"CSF/plasma ratio (Kp, CSF)" refers to the ratio of a compound concentration in cerebrospinal fluid (CSF) vs. in plasma. The ability of a compound to cross blood-brain barrier (BBB) is assessed by measuring its concentrations in CSF and plasma in rodents, and determining the ratio (Kp, CSF).

"Isomers" refer to compounds that have the same molecular formula, but their atomic binding position or spatial arrangement is different. Isomers with different arrangement of their atoms in space are called "stereoisomers". Stereoisomers include optical isomers, geometric isomers, and conformational isomers.

Compounds of the present invention can exist as optical isomers. Optical isomers include enantiomers and diastereomers. An enantiomer is one of two stereoisomers that are mirror images of each other and are non-superposable. A racemic mixture or racemate is one that has equal amounts of left- and right-handed enantiomers of a chiral molecule. Diastereomers are stereoisomers that are not mirror images of one another and are non-superimposable on one another. When a compound is a single isomer and its absolute configuration is determined, it is referred as a "R" or "S" isomer according to the configuration of the substituents around the chiral carbon atom. When its absolute configuration is not determined, it is referred as a (+) or (−) isomer according to its measured optical rotation value. Methods for preparing and separating optical isomers are known to those skilled in the art.

Compounds of the present invention may also have geometric isomers resulting from the distribution of substituents around carbon-carbon double bonds, carbon-nitrogen double bonds, cycloalkyl or heterocyclyl groups. The substituents around the carbon-carbon double bond or carbon-nitrogen bond are designated to be in a Z or E configuration, and the substituents around the cycloalkyl or heterocycle are designated to be in a cis or trans configuration.

Compounds of the present invention may also show tautomerism, such as keto-enol tautomerism.

The present invention includes any tautomeric or stereoisomeric forms and mixtures thereof and is not limited to any tautomeric or stereoisomeric forms used in the compound nomenclature or chemical structural formulae.

"Isotopes" include all stable isotopes of the atoms appearing in the compounds of the present invention. Isotopes include those atoms with the same atomic number but in different masses. Examples of isotopes suitable for incorporation into the compounds of the present invention are isotopes of hydrogen, carbon, nitrogen, oxygen, phosphorus, fluorine and chlorine, for example but not limited to $^{2}H$ (D), $^{3}H$, $^{13}C$, $^{14}C$, $^{15}N$, $^{18}O$, $^{17}O$, $^{31}P$, $^{32}P$, 35S, $^{18}F$ and $^{36}Cl$. The isotopically labeled compounds of the present invention can generally be prepared by conventional techniques known to those skilled in the art or by methods similar to those described in the embodiments using appropriate isotopically labeled reagents instead of non-isotopically labeled reagents. Such compounds have various potential uses, for example, as standards and reagents in the determination of biological activities. In the case of stable isotopes, such compounds have the potential to beneficially alter biological, pharmacological, or pharmacokinetic properties. Deuterium $^{2}H$ (D) is a preferable isotope of the present invention. For example, hydrogen in methyl, methylene or methine can be replaced by deuterium.

Compounds of the present invention can be administered in form of prodrugs. "Prodrugs" refer to derivatives that are converted into biologically active compounds under the physiological condition in vivo, for example, by oxidation, reduction, and hydrolysis (each of which occurs with or without the participation of enzymes). Examples of a prodrug are a compound of the present invention in which an amino is acylated, alkylated or phoshorylated, for example eicosanoyl amino, alanyl amino and pivaloyloxymethyl amino; a hydroxyl is acylated, alkylated or phoshorylated or converted into borate, for example acetoxy, palmitoyloxy, pivaloyloxy, succinyloxy, fumaroyloxy and alanyloxy; a carbonyl is esterified or amidated; and a thiol forms a disulfide bridge with a carrier molecule that selectively delivers the drug to the target and/or to the cytosol of cells, such as peptide. Prodrugs may be prepared from the compounds of the present invention according to well-known methods.

"Pharmaceutically acceptable salts" refer to the salts made from compounds of the present invention with pharmaceutically acceptable bases or acids, including inorganic alkalis or acids and organic bases or acids, under the condition that the compounds contain one or more acidic or basic groups. Compounds of the present invention that contain acidic groups can exist in form of salts, for example, as alkali metal salts, alkaline earth metal salts, or ammonium salts. For example, such salts include sodium salts, potassium salts, calcium salts, magnesium salts or ammonia or organic amine salts such as salts of ethylamine, ethanolamine, triethanolamine or amino acids. Compounds of the present invention that contain basic groups can exist in form of salts as inorganic or organic acid salts. Examples of suitable acids include hydrochloric acid, hydrobromic acid, phosphoric acid, sulfuric acid, nitric acid, methanesulfonic acid, p-toluenesulfonic acid, naphthalene disulfonic acid, oxalic acid, acetic acid, tartaric acid, lactic acid, salicylic acid, benzoic acid, formic acid, propanoic acid, pivalic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to those skilled in the art. If compounds of the present invention contain both acidic and basic groups in the molecule, the present invention further includes internal salts in addition to the mentioned salt forms. Each salt can be obtained by conventional methods known to those skilled in the art, for example by mixing a compound of the present invention with an organic or inorganic acid or base in a solvent or dispersant, or by anion exchange or cation exchange with another salt.

"Pharmaceutical composition" refers to a composition containing one or more of compounds of the present invention or their pharmaceutically acceptable salts, stable isotope derivatives, isomers, prodrugs, and mixtures thereof, and other components such as a pharmaceutically acceptable carrier and excipients.

"Cancer or lymphoma or leukemia" includes but is not limited to B-cell malignancies, B-cell lymphoma, diffuse large B-cell lymphoma, chronic lymphocytic leukemia, small lymphocytic lymphoma, non-Hodgkin Lymphoma (such as ABC-DLBCL), mantle cell lymphoma, follicular lymphoma, Waldenstrom's macroglobulinemia, marginal zone lymphoma, central nervous system lymphoma, chronic lymphocytic lymphoma, B-cell prelymphocytic leukemia, plasma cell lymphoma, multiple myeloma, various solid tumors (such as melanoma, bone cancer, brain cancer, colon cancer, liver cancer, skin cancer, kidney cancer, lung cancer, muscle cancer, bladder cancer, digestive tract/stomach Intestinal cancer, breast cancer, ovarian cancer, head and neck cancer, prostate cancer), etc.

"Autoimmune or inflammatory disease" includes but is not limited to arthritis, multiple sclerosis, osteoporosis, inflammatory bowel disease, colitis, Crohn's disease, lupus, rheumatoid Arthritis, psoriatic arthritis, lupus nephritis, Sjogren's syndrome, IgG4-related diseases, idiopathic thrombocytopenic purpura, immune thrombocytopenia, Wright's syndrome, psoriasis, Behcet's disease, asthma, Pemphigus, diabetes, myasthenia gravis, Guillain-Barre syndrome, Graves' disease, Hashimoto's thyroiditis, vasculitis, autoimmune vasculitis, granuloma with multiple vasculitis, autoimmune hepatitis, etc.

"Therapeutically effective amount" refers to an amount of compounds of the present invention that can effectively inhibit activities of BTK and its C481 mutant, and/or treat or prevent the diseases mediated by BTK and its C481 mutant.

"Patients" refer to mammals, preferably humans.

The present invention relate to two bridged bicyclic compounds A and B (with structures as shown below) as reversible BTK inhibitors, which effectively inhibit the activities of BTK and its C481 mutant, thereby overcoming the drug resistance caused by the C481 mutation associated with irreversible BTK inhibitors.

The present invention is directed to Compounds A, or B, or their pharmaceutically acceptable salts, prodrugs, stable isotope derivatives, isomers and mixtures thereof.

| Compound No. | Compound Structure and Chemical Name |
|---|---|
| A | 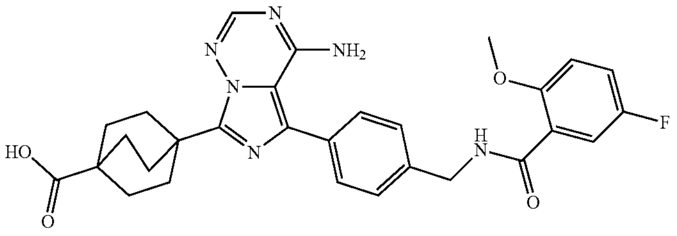 [SMILES: COc1ccc(F)cc1C(=O)NCc1ccc(-c2nc(C34CCC(C(=O)O)(CC3)CC4)n3ncnc(N)c23)cc1] 4-(4-amino-5-(4-((5-fluoro-2-methoxybenzamido)methyl)phenyl)imidazo[5,1-f][1,2,4]triazin-7-yl)bicyclo[2.2.2]octane-1-carboxylic acid |
| B | 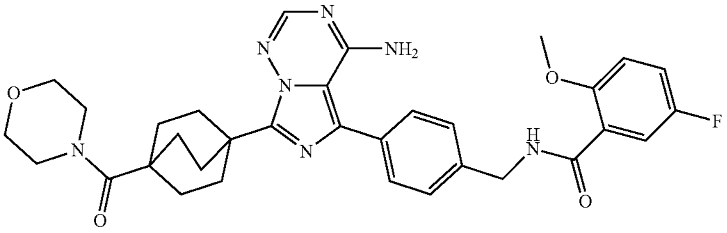 [SMILES: COc1ccc(F)cc1C(=O)NCc1ccc(-c2nc(C34CCC(C(=O)N5CCOCC5)(CC3)CC4)n3ncnc(N)c23)cc1] N-(4-(4-amino-7-(4-(morpholine-4-carbonyl)bicyclo[2.2.2]octan-1-yl)imidazo[5,1-f][1,2,4]triazin-5-yl)benzyl)-5-fluoro-2-methoxybenzamide |

Compound A and B effectively inhibit the activities of BTK and its C481 mutant, having an $IC_{50}$ of less than 10 nM. Compounds A and B are non-brain penetrant, with Kp, CSF less than 0.1.

The present invention also relates to pharmaceutical compositions comprising Compound A or B, or a pharmaceutically acceptable salt, a stable isotope derivative, an isomer and a prodrug thereof, and one or more pharmaceutically acceptable carriers or excipients.

The present invention further relates to a pharmaceutical composition comprising a compound of Formula (I) or its pharmaceutically acceptable salt, stable isotope derivative, isomer, prodrug and a mixture thereof, and at least one additional therapeutic agent, wherein the agent may be a small molecule chemotherapeutic drug (such as anti-inflammatory steroid drug, kinase targeting drug, apoptosis inhibitor, inflammation modulator, cytotoxic drug, DNA damage related drug) or a macromolecular immune and/or inflammation modulator (such as CD-20 antibody, CD19 antibody, PD-1 antibody).

Compound A or B and another therapeutic agent may be present in the same pharmaceutical composition or in different pharmaceutical compositions. Compounds of Formula (I) and another agent may be administered simultaneously or sequentially in the same or different forms.

The present invention provides a method for treating or preventing diseases mediated by BTK or its C481 mutant. The method comprises administering to a patient in need a therapeutically effective amount of Compound A or B, or its pharmaceutically acceptable salts, stable isotope derivatives, isomers, prodrugs and mixtures thereof. The diseases include but are not limited to cancer, lymphoma, leukemia, autoimmune or inflammation diseases, such as B-cell malignancies, B-cell lymphoma, diffuse large B-cell lymphoma, chronic lymphocytic leukemia, small lymphocytic lymphoma, non-Hodgkin's lymphoma (such as ABC-DLBCL), mantle cell lymphoma, follicular lymphoma, Waldenstrom's macroglobulinemia, marginal zone lymphoma, central nervous system lymphoma, chronic lymphocytic lymphoma, B-cell prelymphocytic leukemia, plasma cell lymphoma, multiple myeloma, various solid tumors (such as lung cancer, prostate cancer, head and neck cancer, breast cancer, ovarian cancer, uterine cancer, pancreatic cancer, colon cancer, rectal cancer, stomach cancer, esophageal cancer, brain cancer, liver cancer, kidney cancer, skin cancer, muscle cancer, epithelial cancer, bladder cancer, neuroblastoma, melanoma, bone cancer, melanoma), arthritis, multiple sclerosis, osteoporosis, inflammatory bowel disease, colitis, Crohn's disease, lupus, rheumatoid arthritis, psoriatic arthritis, lupus nephritis, Sjogren's syndrome, IgG4-related diseases, idiopathic thrombocytopenic purpura, immune thrombocytopenia, Wright syndrome, psoriasis, Behcet's disease, asthma, pemphigus, diabetes, myasthenia gravis, Guillain-Barre syndrome, Graves' disease, Hashimoto's thyroiditis, vasculitis, autoimmune vasculitis, granuloma with multiple vasculitis, autoimmune hepatitis, especially B-cell lymphoma, diffuse large B-cell lymphoma, chronic lymphocytic leukemia, small lymphocytic lymphoma, non-Hodgkin's lymphoma (such as ABC-DLBCL), mantle cell lymphoma, filtration alveolar lymphoma, Waldenstrom's macroglobulinemia, marginal zone lymphoma, central nervous system lymphoma, chronic lymphocytic lymphoma, rheumatoid arthritis, systemic lupus erythematosus, multiple sclerosis, lupus nephritis, dryness Syndrome, IgG4-related diseases, idiopathic thrombocytopenic purpura, immune thrombocytopenia, pemphigus, urticaria, etc.

According to the present invention, the pharmaceutical composition may be in any dosage form, including but not limited to tablets, capsules, solutions, freeze-dried preparations and injectable.

The pharmaceutical formulation of the present invention may be administered in form of a dosage unit containing a predetermined amount of active ingredient. Such a unit may contain 1 mg to 1 g, preferably 5 mg to 700 mg, particularly preferably 10 mg to 500 mg of a compound of the present invention, depending on the disease being treated, the method of administration, as well as age, weight, and condition of the patients. The pharmaceutical formulation may be prepared using methods well-known in the pharmaceutical field, for example, by formulating the active ingredient with one or more excipients or one or more adjuvants.

The pharmaceutical formulation of the present invention is suitable for administration by any appropriate method, such as by oral (including oral or sublingual) or parenteral (including subcutaneous, intramuscular, intravenous, or intradermal).

The present invention also provides methods for preparing Compounds A and B. The preparation of compounds of the present invention may be accomplished by the following exemplary methods and examples, but these methods and examples should not be considered as limitation of the scope of the present invention in any way. Compounds of the present invention may also be synthesized by synthetic techniques known to those skilled in the art or by combinations of methods known in the art and of the present invention. The products obtained at each step of reaction are isolated by separation techniques known in the art, including but not limited to extraction, filtration, distillation, crystallization, and chromatographic separation. The starting materials and chemical reagents used for syntheses may be conventionally made based on literature (for example, SciFinder) or purchased.

EXAMPLES

The starting materials in the present invention were synthesized according to methods known in the art or purchased from ABCR GmbH & Co. KG, Acros Organics, Aldrich Chemical Company, Accela ChemBio Inc., Beijing Ouhe, etc.

The structure of a compound was determined by nuclear magnetic resonance (NMR) or mass spectrometry (MS). NMR determination used a Bruker ASCEND-400 NMR spectrometer. The solvent for the determination was deuterated dimethyl sulfoxide (DMSO-$d_6$), deuterated chloroform ($CDCl_3$) or deuterated methanol ($CD_3OD$). The internal standard was tetramethylsilane (TMS) and the chemical shift was given in a unit of $10^{-6}$ (ppm). MS determination used an Agilent SQD (ESI) mass spectrometer (Agilent 6120).

HPLC determination used Agilent 1260 DAD high pressure liquid chromatograph (column: Poroshell120 EC-C18, 50×3.0 mm, 2.7 μm) or Waters Arc high pressure liquid chromatograph (column: Sunfire C18, 150×4.6 mm, 5 μm).

Thin layer chromatography (TLC) used GF254 silica gel plates from Qingdao Haiyang Chemical Co., Ltd. with a thickness of 0.15 to 0.2 mm, and the separation/purification of products by thin layer chromatography used silica plates with a thickness 0.4 to 0.5 mm.

Column chromatography generally used 200 to 300 mesh silica gel from Qingdao Haiyang Chemical Co., Ltd.

Unless otherwise specified in the examples, reactions were run in room temperature (20-30° C.) and under an atmosphere of argon or nitrogen using a balloon with a volume of about 1 L.

Hydrogenation was carried out under an atmosphere of hydrogen using a balloon with a volume of about 1 L that was attached to the reaction vessel after being vacuumed and filled with hydrogen repeatedly for 3 times.

The reaction was monitored using Agilent LCMS (1260/6120) or thin layer chromatography. The solvent eluting systems for column chromatography and TLC included a) dichloromethane/methanol, b) petroleum ether/ethyl acetate, or other systems as indicated. The ratio of the solvents was adjusted according to the polarity of the compound, and further adjusted by addition of a small amount of TEA, or an acidic or alkaline reagent as needed. The compound purification was alternatively done using Waters' MS-guided automated preparation system (abbreviated as prep-HPLC) with a MS detector (SQD2), eluting at a flow rate of 20 mL/min in an appropriate acetonitrile/water (containing 0.1% TFA or formic acid) or acetonitrile/water (containing 0.05% of 25-28% ammonium hydroxide) gradient (XBridge-C18, 19×150 mm, 5 μm). Some compounds were prepared as HCl salts after prep-HPLC purification by addition of 1 N HCl to the collected fractions, followed by drying under reduced pressure.

The abbreviation DMF refers to N,N-dimethylformamide.

The abbreviation DIPEA refers to N,N-diisopropylethylamine.

The abbreviation DBU refers to 1,8-diazabicycloundec-7-ene.

The abbreviation NIS refers to N-iodosuccinimide.

$Pd(dppf)Cl_2$ refers to [1,1'-bis(diphenylphosphino)ferrocene]dichloropalladium.

The abbreviation HATU refers to 2-(7-azabenzotriazole)-N,N,N',N'-tetramethylurea hexafluorophosphate.

Example 1. Preparation of 4-(4-amino-5-(4-((5-fluoro-2-methoxybenzamido)methyl)phenyl)imidazo[5,1-f][1,2,4]triazin-7-yl)bicyclo[2.2.2]octane-1-carboxylic acid (Compound A)

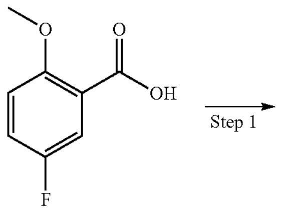

1a

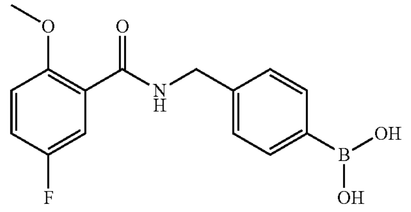

1b

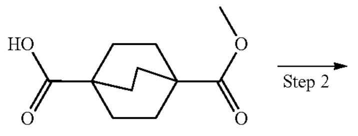

1c

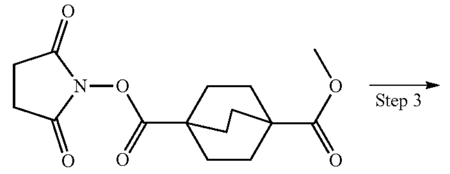

1d

-continued

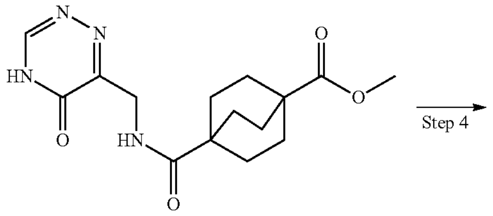

1e

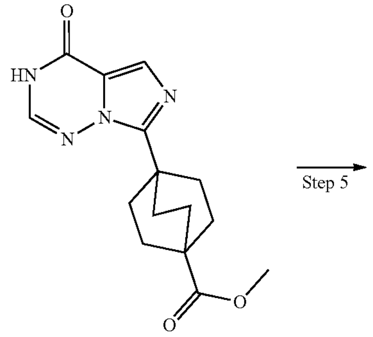

1f

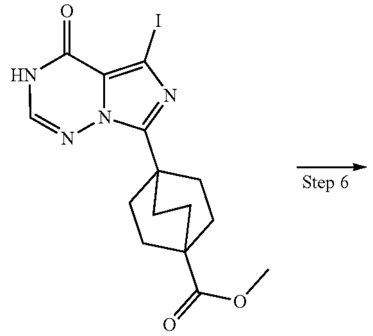

1g

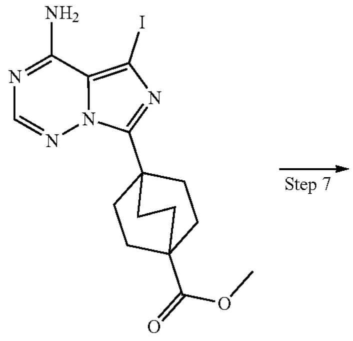

1h

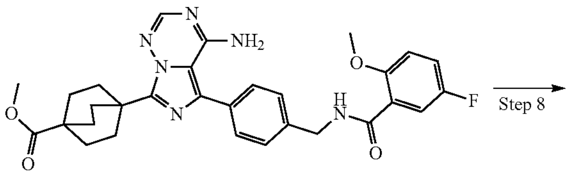

1i

-continued

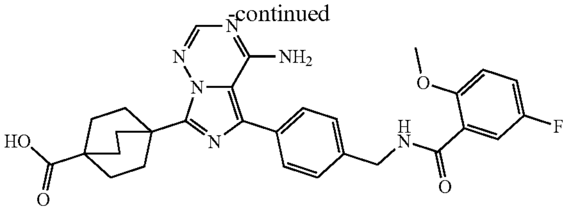

A

Step 1. (4-((5-fluoro-2-methoxybenzamido)methyl) phenyl)boronic acid (1b)

To a solution of 5-fluoro-2-methoxybenzoic acid 1a (340 mg, 2 mmol) and DMF (0.05 mL) in dichloromethane (10 mL) at 0° C. was added oxalyl chloride (279 mg, 2.2 mmol). The mixture was gradually warmed to room temperature and stirred for 1 hour, then cooled to 0° C. again, and added with a suspension of (4-(aminomethyl)phenyl)boronic acid hydrochloride (374 mg, 2 mmol) and DIPEA (516 mg, 4 mmol) in THF (20 mL). After stirring at room temperature for 15 hours, the solvent was removed under reduced pressure. The residue was dissolved in ethyl acetate (100 mL), washed with saturated ammonium chloride (50 mL) and brine (50 mL), dried over anhydrous sodium sulfate, and filtered. The filtrate was concentrated under reduced pressure to give the title compound 1b (460 mg, 76%).

MS m/z (ESI): 304 [M+1]

Step 2. 1-(2,5-dioxopyrrolidin-1-yl) 4-methyl bicyclo[2.2.2]octane-1,4-dicarboxylate (1d)

To a solution of (methoxycarbonyl)bicyclo[2.2.2]octane-1-carboxylic acid 1c (850 mg, 4 mmol) and 1-hydroxypyrrolidine-2,5-dione (552 mg, 4.8 mmol) in THF (50 mL) at 0° C. was added DCC (1.07 g, 5.2 mmol). After warming to room temperature and stirring for 15 hours, the mixture was cooled to 0° C. and filtered. The filtrate was concentrated to dryness to give the title compound 1d (1.4 g, crude).

MS m/z (ESI): 310 $[M+H]^+$

Step 3. methyl 4-(((5-oxo-4,5-dihydro-1,2,4-triazin-6-yl)methyl)carbamoyl)bicyclo[2.2.2]octane-1-carboxylate (1e)

To a solution of 6-aminomethyl-4H-[1,2,4]triazin-5-one (252 mg, 2 mmol) and DIPEA (1.03 g, 8 mmol) in DMF (5 mL) was added a solution of 1d (1.4 g, crude) in THF (5 mL) dropwise. The mixture was stirred for 3 hours and then concentrated to dryness. The residue was purified by silica gel column chromatography (dichloromethane/methanol=50/1 to 10/1) to give the title compound 1e (150 mg, 23% over 2 steps).

MS m/z (ESI): 321 $[M+H]^+$

Step 4. methyl 4-(4-oxo-3,4-dihydroimidazo[5,1-f][1,2,4]triazin-7-yl)bicyclo[2.2.2]octane-1-carboxylate (1f)

To a solution of 1e (150 mg, 0.47 mmol) in MeCN (10 mL) was added $POCl_3$ (2 mL). The mixture was heated to 80° C. and stirred for 5 hours. The mixture was then concentrated to dryness to give the title compound 1f (150 mg, 100%).

MS m/z (ESI): 303 $[M+H]^+$

Step 5. methyl 4-(5-iodo-4-oxo-3,4-dihydroimidazo[5,1-f][1,2,4]triazin-7-yl)bicyclo[2.2.2]octane-1-carboxylate (1g)

To a solution of 1f (150 mg, crude, 0.47 mmol) in DMF (5 mL) was added NIS (529 mg, 2.35 mmol). The mixture was heated to 55° C. and stirred for 5 hours. After cooling to room temperature, the mixture was purified by prep-HPLC to give the title compound 1g (80 mg, 40%).

MS m/z (ESI): 429 $[M+H]^+$

Step 6. methyl 4-(4-amino-5-iodoimidazo[5,1-f][1,2,4]triazin-7-yl)bicyclo[2.2.2]octane-1-carboxylate (1h)

To a solution of 1H-[1,2,4]triazole (131 mg, 1.9 mmol) in pyridine (2 mL) was added $POCl_3$ (86 mg, 0.56 mmol). The mixture was stirred for 10 minutes and added with a solution of 1g (80 mg, 0.19 mmol) in pyridine (2 mL). After stirring for another 1 hour, the mixture was added with a solution of $NH_3$ (2 M in isopropanol, 10 mL) and stirred for 0.5 hour. The mixture was then concentrated to dryness and the residue was purified by prep-HPLC to give the title compound 1h (60 mg, 74%).

MS m/z (ESI): 428 $[M+H]^+$

Step 7. methyl 4-(4-amino-5-(4-((5-fluoro-2-methoxybenzamido)methyl)phenyl)imidazo[5,1-f][1,2,4]triazin-7-yl)bicyclo[2.2.2]octane-1-carboxylate (1i)

A mixture of 1h (60 mg, 0.14 mmol), 1b (64 mg, 0.21 mmol), $K_2CO_3$ (39 mg, 0.28 mmol), $Pd(dppf)Cl_2$ (11 mg, 0.014 mmol), 1,4-dioxane (4 mL) and water (1 mL) was heated to 100° C. under nitrogen atmosphere and stirred for 2 hours. After cooling to room temperature, the mixture was concentrated to dryness and the residue was purified by silica gel column chromatography (petroleum ether/EtOAc=20:1 to 1:2) to give the title compound 1i (60 mg, 77%).

MS m/z (ESI): 559 $[M+H]^+$.

$^1$H NMR (400 MHz, $CD_3OD$) δ 7.80 (s, 1H), 7.64-7.57 (m, 3H), 7.52 (d, J=8.3 Hz, 2H), 7.25 (ddd, J=9.1, 7.6, 3.3 Hz, 1H), 7.17 (dd, J=9.1, 4.2 Hz, 1H), 4.69 (s, 2H), 3.96 (s, 3H), 3.66 (s, 3H), 2.26 (dd, J=9.7, 6.2 Hz, 6H), 1.93 (dd, J=9.7, 6.3 Hz, 6H).

Step 8. 4-(4-amino-5-(4-((5-fluoro-2-methoxybenzamido)methyl)phenyl)imidazo[5,1-f][1,2,4]triazin-7-yl)bicyclo[2.2.2]octane-1-carboxylic acid (A)

To a solution of 1i (55 mg, 0.098 mmol) in THF (10 mL) was added lithium hydroxide solution (1 N, 4 mL). The mixture was heated to 40° C. and stirred for 48 hours. After cooling to room temperature, the reaction mixture was added with glacial acetic acid (1 mL) and extracted with ethyl acetate (2×50 mL). The combined organic phase was dried over anhydrous sodium sulfate, filtered, and concentrated under reduced pressure. The residue was purified by prep-HPLC to give the title compound A (40 mg, solid, 75%).

MS m/z (ESI): 545 [M+1]

$^1$H NMR (400 MHz, $CD_3OD$) δ 7.80 (s, 1H), 7.64-7.56 (m, 3H), 7.53 (d, J=8.1 Hz, 2H), 7.28-7.22 (m, 1H), 7.17 (dd, J=9.1, 4.2 Hz, 1H), 4.69 (s, 2H), 3.96 (d, J=7.6 Hz, 3H), 2.30-2.22 (m, 6H), 1.98-1.90 (m, 6H).

Example 2. Preparation of N-(4-(4-amino-7-(4-(morpholine-4-carbonyl)bicyclo[2.2.2]octan-1-yl)imidazo[5,1-f][1,2,4]triazin-5-yl)benzyl)-5-fluoro-2-methoxybenzamide (Compound B)

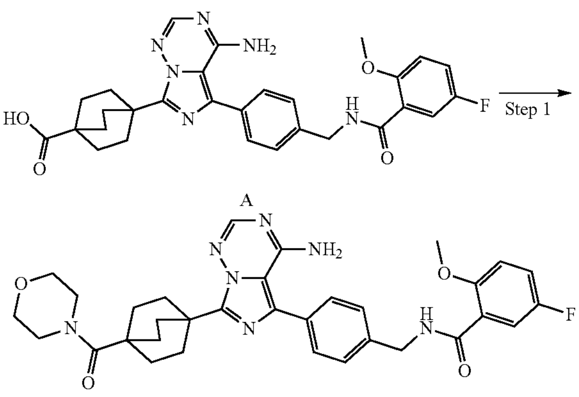

A

B

To a solution of A (75 mg, 0.137 mmol), morpholine (12 mg, 0.137 mmol) and DIPEA (53 mg, 0.409 mmol) in DMF (5 mL) was added HATU (58 mg, 0.151 mmol). The resulting mixture was stirred for 5 minutes and then purified by prep-HPLC to give the title compound B (40 mg, solid, 48%).

MS m/z (ESI): 614.2 [M+H]+

$^1$H NMR (400 MHz, DMSO-$d_6$) δ 8.84 (t, J=6.0 Hz, 1H), 7.88 (s, 1H), 7.58 (d, J=8.2 Hz, 2H), 7.52 (dd, J=9.2, 3.3 Hz, 1H), 7.46 (d, J=8.2 Hz, 2H), 7.39-7.29 (m, 1H), 7.19 (dd, J=9.1, 4.3 Hz, 1H), 4.57 (d, J=6.1 Hz, 2H), 3.90 (s, 3H), 3.57 (d, J=9.6 Hz, 8H), 2.21-2.09 (m, 6H), 1.97-1.84 (m, 6H).

Example 3. BTK Activity Inhibition Assay

In vitro kinase assay was used to evaluate the effects of compounds of the present invention on BTK activity (Table 1).

The experimental method is summarized below:

By using the homogeneous time-resolved fluorescence (HTRF) kinase detection kit (Cisbio, catalog number 62TK0PEC), the enzymatic activity of BTK is determined by detecting the phosphorylation level of the substrate in the kinase reaction. The reaction buffer contains the enzyme reaction buffer (1×) from the kit, 5 mM $MgCl_2$, 1 mM DTT, 10 nM SEB and 0.01% Tween-20; the kinase reaction solution contains human-derived recombinant BTK protein (Carna Biosciences, Catalog No. 08-180) diluted to 0.2 ng/μL with the reaction buffer; the substrate reaction solution contains biotin-labeled tyrosine kinase substrate diluted to 0.5 μM with the reaction buffer and 40 μM ATP; the detection buffer contains $Eu^{3+}$-labeled cage antibody diluted to 0.05 ng/μL and streptavidin-labeled XL665 antibody diluted to 31.25 nM with the reaction buffer; the test compound is dissolved and diluted to 100 μM with DMSO, followed by a 4-fold serial dilution with DMSO to the lowest concentration of 6.1 nM and finally 40-time dilution with the reaction buffer for each concentration point. If the $IC_{50}$ value of the compound is very low, the initial concentration of the compound is reduced.

Add 4 μL test compound solution and 2 μL kinase reaction solution to a 384-well detection plate (Corning, catalog number 3674), mix well and incubate at room temperature for 15 minutes; add 4 μL substrate reaction solution and incubate for 50 minutes; add 10 μL detection buffer, mix well and stand for 60 minutes; detect signal at 620 nm and 665 nm using an Envision plate reader (Perkin Elmer). The signal value (absorbance at 665 nm/absorbance at 620 nm) is positively correlated with the degree of phosphorylation of the substrate, thereby detecting the kinase activity of BTK. In this experiment, the group without BTK is the negative control (100% inhibition) and the group with BTK but no compound is the positive control (0% inhibition). The inhibition curve is plotted and the corresponding $IC_{50}$ value of the test compound is calculated using XLfit software (ID Business Solutions Ltd., UK).

Example 4. BTK C481S Activity Inhibition Assay

In vitro kinase assay was used to evaluate the effects of compounds of the present invention on BTK C481S activity (Table 1).

The experimental method is summarized below:

By using the homogeneous time-resolved fluorescence (HTRF) kinase detection kit (Cisbio, catalog number 62TK0PEC), the enzymatic activity of BTK C481S is determined by detecting the phosphorylation level of the substrate in the kinase reaction. The reaction buffer contains the enzyme reaction buffer (1×) from the kit, 5 mM $MgCl_2$, 1 mM DTT, 10 nM SEB, and 0.01% Tween-20; the kinase reaction solution contains human recombinant BTK C481S protein (purified in-house) diluted to 1.5 ng/μL with the reaction buffer; the substrate reaction solution contains biotin-labeled tyrosine kinase substrate diluted to 0.5 μM with the reaction buffer and 35 μM ATP; the detection buffer contains $Eu^{3+}$-labeled cage antibody diluted to 0.05 ng/μL and streptavidin-labeled XL665 antibody diluted to 31.25 nM with the reaction buffer; the test compound is dissolved and diluted to 100 μM with DMSO, followed by a 4-fold serial dilution with DMSO to the lowest concentration of 6.1 nM and finally 40-time dilution with the reaction buffer for each concentration point. If the $IC_{50}$ value of the compound is very low, the initial concentration of the compound is reduced.

Add 4 μL test compound solution and 2 μL kinase reaction solution to a 384-well detection plate (Corning, catalog number 3674), mix well and incubate at room temperature for 15 minutes; add 4 μL substrate reaction solution and incubate for 50 minutes; add 10 μL detection buffer, mix well and stand for 60 minutes; detect signal at 620 nm and 665 nm using an Envision plate reader (Perkin Elmer). The signal value (absorbance at 665 nm/absorbance at 620 nm) is positively correlated with the degree of phosphorylation of the substrate, thereby detecting the kinase activity of BTK C481S. In this experiment, the group without BTK is the negative control (100% inhibition) and the group with BTK C481S but no compound is the positive control (0% inhibition). The inhibition curve is plotted and the corresponding $IC_{50}$ value of the test compound is calculated using XLfit software (ID Business Solutions Ltd., UK).

Table 1 shows the results of BTK $IC_{50}$ and BTK C481S $IC_{50}$ of Compound A and B.

TABLE 1

| Compound No. | BTK $IC_{50}$ (nM) | BTK C481S $IC_{50}$ (nM) |
|---|---|---|
| A | 0.7 | 1.3 |
| B | 1.0 | 1.2 |

Example 5. Brain Penetration Activity Test

Compound A or B in a 0.5 mg/mL solution containing 5% N,N-dimethylacetamide+10% solutol+85% saline was orally administered to twelve male Sprague Dawley rats at a dose of 5 mg/kg. Samples of plasma, brain tissue homogenate (for measuring Kp, brain) and cerebrospinal fluid (for measuring Kp, CSF) were collected at 1, 2, 4 and 8 hours after administration (from three animals at each time point).

The concentrations of the compound in plasma, brain tissue homogenate, and CSF were quantified by LC-MS/MS using an API-4500 mass spectrometer, respectively. The limit of quantification (LOQ) of analysis was 1 ng/mL. The pharmacokinetic (PK) parameters were calculated by the non-compartmental method using WinNonlin. Each of Kp, brain and Kp, CSF was calculated as AUCbrain/AUCplasma and AUCCSF/AUCplasma, respectively. The results are shown in Table 2, which shows that both Compounds A and B are non-brain penetrants.

TABLE 2

| Compound No. | $K_p$, brain | $K_p$, CSF |
|---|---|---|
| A | 0.0355 | 0.0054 |
| B | 0.0315 | 0.0043 |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. Compound A, or B, or a pharmaceutically acceptable salt, stable isotope derivative, or stereoisomer thereof:

A

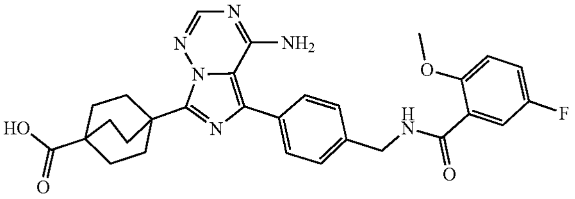

B

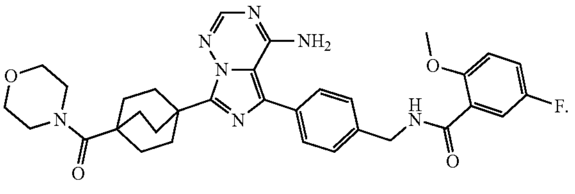

.

2. The compound of claim 1, which is Compound A.

3. A pharmaceutical composition comprising the compound of claim 2, or a pharmaceutically acceptable salt, stable isotope derivative, or stereoisomer thereof, and a pharmaceutically acceptable carrier thereof.

4. The compound of claim 1, which is Compound B.

5. A pharmaceutical composition comprising the compound of claim 4, or a pharmaceutically acceptable salt, stable isotope derivative, or stereoisomer thereof, and a pharmaceutically acceptable carrier thereof.

* * * * *